(12) United States Patent
Shinder-Lerner

(10) Patent No.: US 9,437,996 B2
(45) Date of Patent: Sep. 6, 2016

(54) ROTARY ELECTRICAL INTERCONNECT DEVICE

(71) Applicant: Hypertronics Corporation, Hudson, MA (US)

(72) Inventor: Arkady Shinder-Lerner, Framingham, MA (US)

(73) Assignee: Hypertronics Corporation, Hudson, MA (US)

( * ) Notice: Subject to any disclaimer, the term of this patent is extended or adjusted under 35 U.S.C. 154(b) by 0 days.

(21) Appl. No.: 14/692,653

(22) Filed: Apr. 21, 2015

(65) Prior Publication Data

US 2015/0229086 A1    Aug. 13, 2015

Related U.S. Application Data

(63) Continuation of application No. 14/069,752, filed on Nov. 1, 2013, now Pat. No. 9,039,423.

(60) Provisional application No. 61/721,433, filed on Nov. 1, 2012.

(51) Int. Cl.
*H01R 39/00* (2006.01)
*H01R 39/64* (2006.01)
*H01R 43/10* (2006.01)
(Continued)

(52) U.S. Cl.
CPC ............ *H01R 39/64* (2013.01); *H01R 39/08* (2013.01); *H01R 39/18* (2013.01); *H01R 43/10* (2013.01); *Y10T 29/49208* (2015.01)

(58) Field of Classification Search
CPC ...... H01R 35/04; H01R 39/64; H01R 39/00; H01R 39/646; H01R 39/08; H02K 5/225; H02K 13/006; F05B 2220/7066

USPC ............ 439/11, 13, 20–24, 28; 310/71, 128, 310/219, 231, 232

See application file for complete search history.

(56) References Cited

U.S. PATENT DOCUMENTS

| | | | |
|---|---|---|---|
| 3,297,973 A | 1/1967 | Wendell | |
| 4,080,540 A * | 3/1978 | Karube | ............... H02K 37/10 310/154.04 |
| 4,329,606 A * | 5/1982 | Montagu | ............... H02K 9/22 310/112 |

(Continued)

FOREIGN PATENT DOCUMENTS

| | | |
|---|---|---|
| EP | 2019460 | 10/2011 |
| EP | 2451028 | 5/2012 |
| EP | 2515392 | 10/2012 |

*Primary Examiner* — Thanh Tam Le
(74) *Attorney, Agent, or Firm* — Snell & Wilmer LLP

(57) ABSTRACT

A rotary device for providing continuous electrical connections between dynamic, rotationally engaged connector components. The rotary device includes a rotor assembly comprising a plurality of slip ring elements electrically connected to a connector or cable at the rotor end of the device. The rotary device also includes a stator assembly configured to receive the rotor assembly, with slide contacts electrically connected to a connector or cable at the stator end of the device. The rotor assembly is rotationally coupled to the stator assembly, and the slip rings and slide contacts maintain electrical contact during rotation of the rotor assembly relative to the stator assembly. A first electronic device and a second electronic device connected using the rotary device can be freely rotated without twisting of the cable between the two devices. A method for assembling a rotary device configured based on the devices to be connected.

20 Claims, 13 Drawing Sheets

(51) Int. Cl.
  *H01R 39/08*  (2006.01)
  *H01R 39/18*  (2006.01)

(56) References Cited

U.S. PATENT DOCUMENTS

| | | | |
|---|---|---|---|
| 5,483,116 A * | 1/1996 | Kusase | H02K 21/044 |
| | | | 310/156.66 |
| 5,923,114 A | 7/1999 | Senni | |
| 6,949,847 B2 | 9/2005 | Tsutsumi et al. | |
| 7,119,471 B2 | 10/2006 | Kiderman et al. | |
| 7,215,052 B2 * | 5/2007 | Blase | F02M 37/08 |
| | | | 310/254.1 |
| 7,307,367 B2 | 12/2007 | Angerpointner et al. | |
| 7,663,285 B2 * | 2/2010 | Yumoto | H02K 3/522 |
| | | | 310/194 |
| 7,701,108 B2 | 4/2010 | Yu et al. | |
| 7,750,516 B2 | 7/2010 | Elser et al. | |
| 8,106,562 B2 | 1/2012 | Krogh et al. | |
| 8,461,733 B2 * | 6/2013 | Takechi | H02K 11/048 |
| | | | 310/257 |
| 8,499,438 B2 * | 8/2013 | Agapiou | H02K 15/0081 |
| | | | 29/597 |
| 8,729,755 B2 * | 5/2014 | Nakagawa | H02K 3/522 |
| | | | 310/68 R |
| 8,899,991 B2 | 12/2014 | Ickler | |
| 8,922,080 B2 * | 12/2014 | Nakagawa | H02K 3/00 |
| | | | 310/71 |
| 9,021,684 B2 * | 5/2015 | Lenker | H01R 43/10 |
| | | | 29/596 |
| 2005/0012420 A1 | 1/2005 | Kiderman et al. | |
| 2009/0091208 A1 | 4/2009 | Yu et al. | |
| 2011/0210644 A1 | 9/2011 | Krogh et al. | |
| 2012/0270415 A1 | 10/2012 | Lenker et al. | |

* cited by examiner

ROTARY ELECTRICAL INTERCONNECT DEVICE

CROSS REFERENCE TO RELATED APPLICATIONS

This application is a continuation of U.S. application Ser. No. 14/069,752, entitled "Rotary Electrical Interconnect Device," filed on Nov. 1, 2013, which claims the benefit and priority of U.S. Provisional Application No. 61/721,433, entitled "Rotary Electrical Interconnect Device," filed on Nov. 1, 2012, the disclosures of the Non-Provisional and Provisional Applications are hereby incorporated by reference herein in their entirety.

BACKGROUND

1. Field

The present invention relates generally to electrical connectors and improvements thereto. More particularly, the present invention relates to rotary electrical interconnect devices that are configured to maintain an electrical connection through a rotatable interface.

2. Description of the Related Art

Electrical connectors that permit one component of the connector to rotate with respect to a second component of the connector while maintaining an electrical connection between the components are used in a variety of technical fields and applications. These connections, referred to as slip rings, are employed in applications such as cable reels, turbines, motors, remote video devices, robotics, and other devices requiring transmission of electrical power or signal through a rotating or rotatable electrical connection system.

Slip rings transfer electrical signals through a rotatable electrical contact using a conductive ring mounted on a rotary member. The conductive ring is in sliding contact with a conductive brush mounted to a second component of the connector. Rotating electrical connectors having various configurations based on this type of electrical contact have been developed. However, they are generally subject to drawbacks such as high complexity and manufacturing costs, low reliability and poor performance, and a lack of capacity for customization or scaling according to the requirements of a particular electronic system.

Advances in the medical field have led to an increasing variety and complexity of procedures that can be performed using devices that are inserted into the body of a patient. For example, a growing number of minimally invasive medical and surgical procedures can be performed endovascularly, laproscopically, endoscopically, or robotically using catheters, endoscopes and other insertable medical devices. These devices frequently have an electronic component requiring an electrical connection to external devices that can support a number of discrete electronic connections or circuits for transmittance of signal and power. The cables required to make connections to devices inserted within a patient or any other remote and/or constrained space, combined with the manipulations that may be necessary in the course of performing a procedure, such as twisting or rotational movement of the remote device, can lead to twisting, kinking, jamming or similar problems with the associated electronic cabling. Therefore, a need exists for an improved rotary electrical connector suitable for use in catheters and the like that would allow for independent rotation of connected devices while providing for uninterrupted electronic signals.

SUMMARY

A rotary electrical interconnect device utilizing components that may be modularly assembled using simple and robust mechanical connections is disclosed.

In various embodiments, a rotary device for providing electrical connections between two or more electronic components includes a rotor assembly and a stator assembly. The rotor assembly may include a rotor shaft, a rotor assembly coupler, and a plurality of slip ring elements. Each slip ring element may further comprise a slip ring mounted on an insulator disc, with each insulator disc having a slip ring portion with a first circumference, a spacer portion with a second circumference greater than that of the slip ring portion, and a hub configured to receive the rotor shaft and connected to the slip ring portion and the spacer portion by support arms. The rotor assembly may also include a plurality of rotor assembly leads, with each electrically connected to a slip ring. The stator assembly is configured to rotationally engage the rotor assembly coupler and includes a stator having a cavity and configured to receive the rotor assembly, a plurality of slide contacts, and a plurality of stator assembly leads, each electrically connected to a slide contact. The rotary device may also include a housing configured to cover the rotary device.

In various embodiments, a rotary device may be configured as a cable-to-cable rotary device, a connector-to-connector rotary device, or a connector-to-cable rotary device. A cable-to-cable rotary device may include fittings or other features for attaching a cable sheath to an end of the rotary device housing or to an end of the rotor assembly or stator assembly. A cable-to-cable rotary device may be connected to a cable sheath at the rotor end and the stator end of the housing, and the rotor assembly leads and the stator assembly leads may extend outward from the rotary device to a remote device or connector through the connected cable sheath. A connector-to-connector rotary device may include a connector at the rotor end and the stator end of the rotary device. The connectors may be electrically connected to the rotor assembly leads and the stator assembly leads and be used to electrically connect the rotary device to remote devices using complementary connectors. A connector-to-cable rotary device includes both a connector and a cable sheath connection at ends of the rotary device, as described above.

In various embodiments, a method of assembling a rotary device is disclosed. A method of assembling a customized rotary device based on the electrical connection requirements of the electronic components to be connected may include assembling a plurality of slip ring elements, placing the plurality of slip ring elements onto a rotor shaft, securing the plurality of slip ring elements to form a rotor assembly, assembling a stator onto the rotor assembly, connecting a plurality of slide contacts to the stator such that each of the plurality of slide contacts electrically connects to each of the plurality of slip ring elements respectively, connecting a plurality of stator assembly leads to the plurality of slide contacts respectively to form a stator assembly, and covering the stator assembly with a housing.

In various embodiments, a method may also include determining the number of electrical channels required by the components to be connected, as well as the electrical specification requirements for each channel. A method may further include selecting a rotor assembly and a stator assembly of the appropriate sizes. A method may also include selecting components having the desired ends, such as cable sheath connection ends or connector ends. A method may further include selecting and assembling the rotor assembly components into a completed rotor assembly based on the requirements of the system to be connected, followed by installation of the rotor assembly in the stator. A method may also include assembly of the stator assembly, attachment of the connector ends, installation of the rotary device housing, and attachment of cable sheath.

BRIEF DESCRIPTION OF THE DRAWINGS

Other systems, methods, features, and advantages of the present invention will be or will become apparent to one with skill in the art upon examination of the following figures and detailed description. It is intended that all such additional systems, methods, features, and advantages be included within this description, be within the scope of the present invention, and be protected by the accompanying claims. Component parts shown in the drawings are not necessarily to scale, and may be exaggerated to better illustrate the important features of the present invention. In the drawings, like reference numerals designate like parts throughout the different views, wherein:

DETAILED DESCRIPTION

Figure 1A:
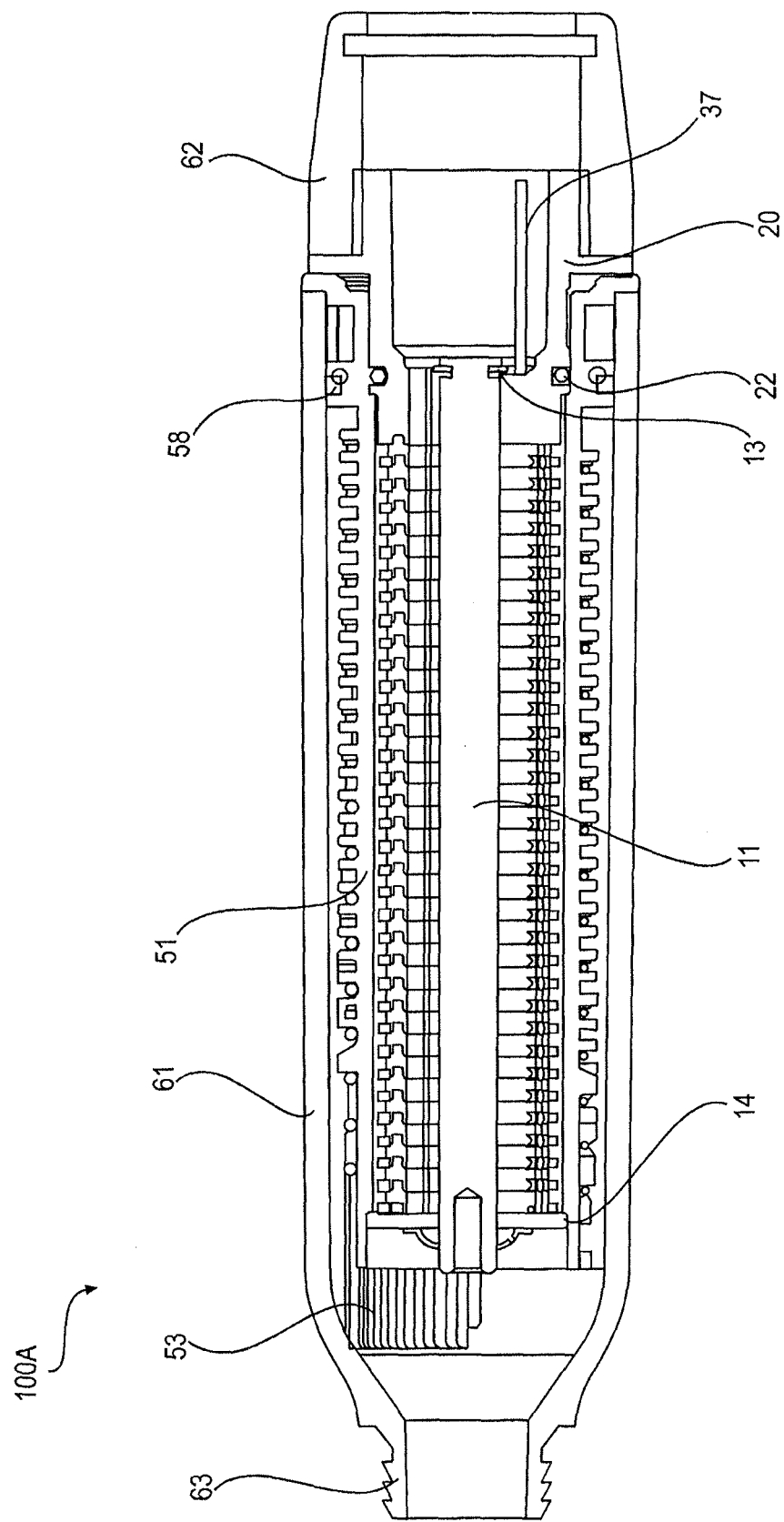
FIG. 1A is a cut-away side view of a cable-to-cable rotary device in accordance with various embodiments (cables not shown)
Figure 1B:
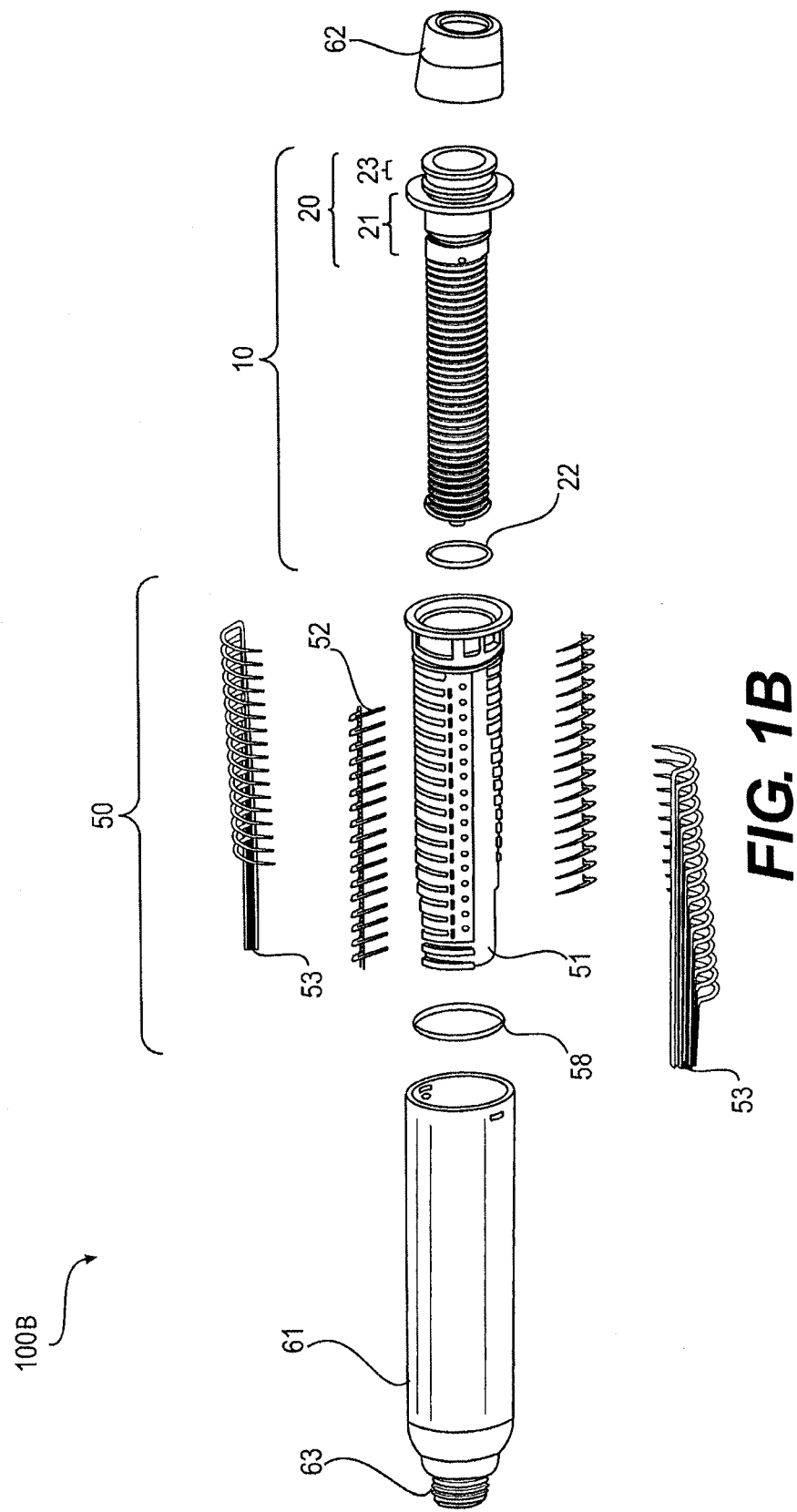
FIG. 1B is an exploded view of a cable-to-cable rotary device in accordance with various embodiments (cables not shown)
Figure 2A:
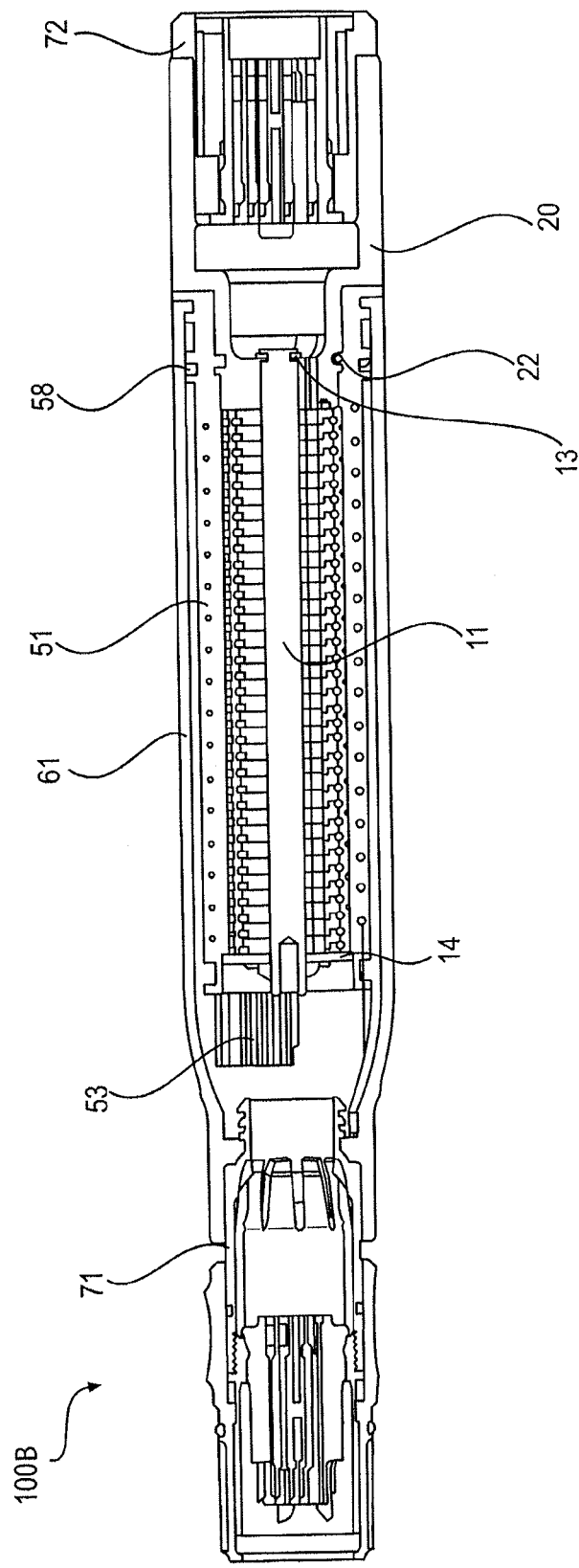
FIG. 2A is a cut-away side view of connector-to-connector rotary device in accordance with various embodiments.
Figure 2B:
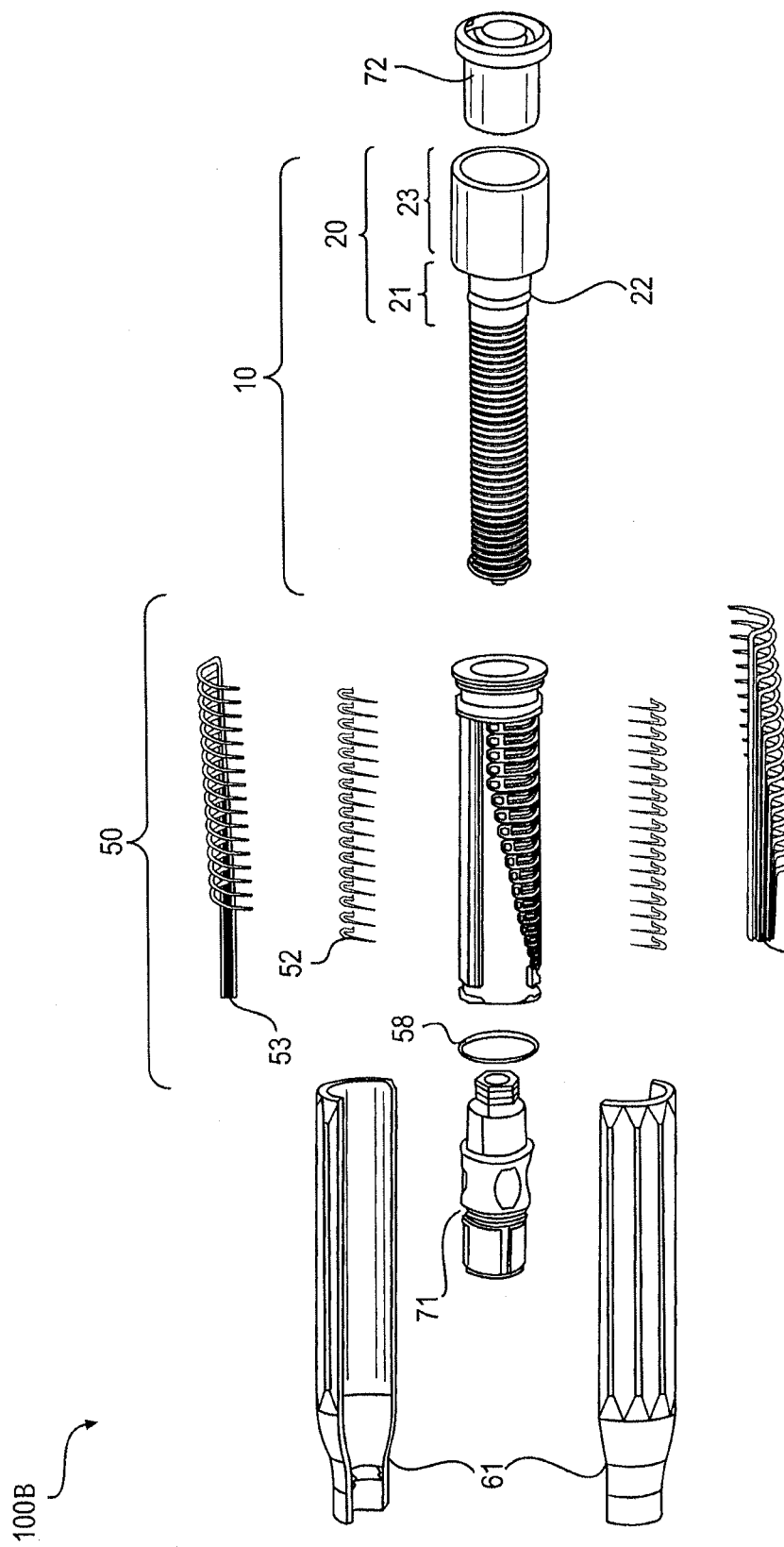
FIG. 2B is an exploded view of a connector-to-connector rotary device in accordance with various embodiments.

Referring first to FIGS. 1A-2B, cut-away side views and exploded views of rotary devices in accordance with various embodiments are shown. FIGS. 1A and 1B show a cable-to-cable rotary device 100A, and FIGS. 2A and 2B show a connector-to-connector rotary device 100B. Rotary devices 100A and 100B share various features of rotary devices in accordance with embodiments of the present disclosure that are described in greater detail below.

Figure 3:
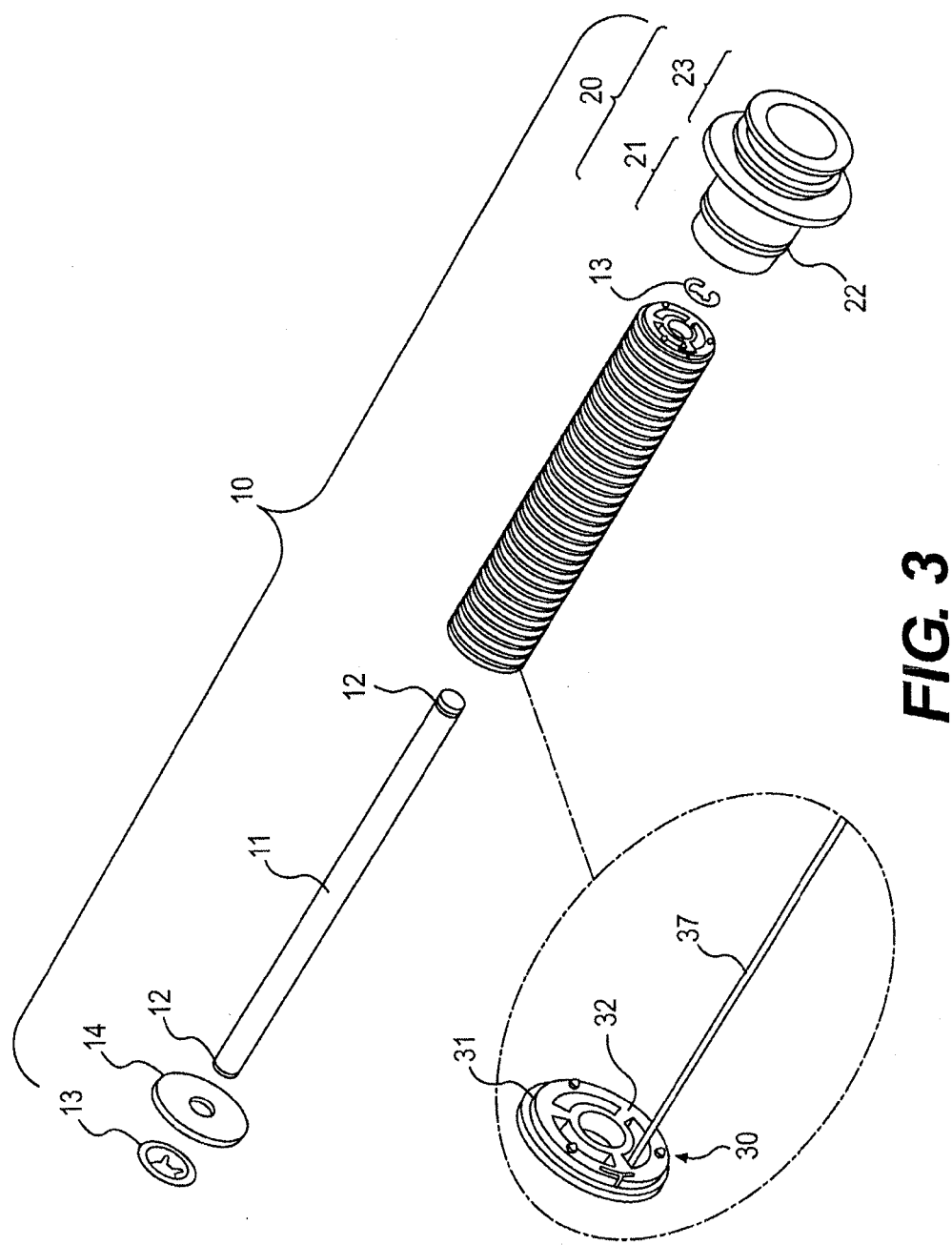
FIG. 3 is an exploded view of a rotor assembly with 34 slip ring elements in accordance with various embodiments.

With continued reference to FIGS. 1A-2B, as well as to FIG. 3, a rotary device includes a rotor assembly 10. Each rotor assembly 10 includes a rotor shaft 11. The shaft may be formed or machined from of any of a variety of suitable materials, including both conductive and non-conductive materials, for example, metals or metal alloys, ceramics, or plastics. In various embodiments and as illustrated in FIG. 3, a rotor shaft 11 may be cylindrical with a substantially smooth or uniform surface. In other embodiments, the shaft may have features to facilitate operative connection of the shaft to other components of the rotor assembly or operative connection of the rotor assembly to the stator assembly. For example, the rotor shaft may have one or more longitudinal grooves, splines, or keys that engage a corresponding pattern in the hub of a slip ring element or other component of the rotor assembly.

Similarly, a rotor shaft may have transverse holes or grooves suitable for use with various retention devices, such as lock rings, retaining rings, snap rings, circlips, retention pins, or the like, that may be used to retain rotor assembly components such as slip ring elements or bearings on the rotor shaft. In various embodiments and as illustrated in FIG. 3, a rotor shaft 11 may have grooves 12 located adjacent to the ends of the rotor shaft that are suitable for use with retaining rings 13 which may be used to attach or retain various other components of the rotor assembly, such as a bearing 14. In other embodiments, one or both ends of a rotor shaft may be threaded or otherwise shaped or contoured to mechanically engage a complementary portion of a rotary device, such as by a threaded connection, press-fit, or other interference connection. Rotor shafts having any type of feature suitable for connecting or engaging any other type of rotor assembly component or rotary device component along its length or at an end are within the scope of the present disclosure.

A rotor assembly 10 may also include a rotor assembly coupler 20 connected to an end of the rotor shaft 11. A rotor assembly coupler 20 may be substantially cylindrical in shape and define an inner cavity with a substantially open end oriented outward from the rotary device and a second end with an axial hub defining a smaller opening suitable for receiving an end of a rotor shaft 11. A rotor assembly coupler 20 may be connected to a rotor shaft 11 using any suitable means, including, for example, a threaded, press-fit, or other interference connection. As illustrated in the rotor assembly 10 shown in FIG. 3, the rotor shaft 11 may be configured with a circumferential groove 12 adjacent an end of the shaft which is inserted into the axial hub of the rotor assembly coupler 20 and fit with a retaining ring 13 which serves to retain an end of the rotor shaft 11 in the rotor assembly coupler.

A rotor assembly coupler 20 may also include a stator interface portion 21 with an outer surface configured to fit an interior portion of the stator 51. The stator interface portion 21 may further include an o-ring 22 or other gasket, packing, or seal to sealably engage the inner surface of a stator during rotation of the rotor assembly coupler 20 with respect to a stator 51. Similarly, in various embodiments, the stator interface portion 21 of a rotor assembly coupler 20 may serve as a bearing such as an integral plain bearing or friction bearing and provide a surface for rotational engagement of an interior portion of the stator. In other embodiments, a rotor assembly coupler 20 or stator interface portion 21 may also include a separate bearing to facilitate rotational engagement of a rotor assembly with a stator of a rotary device. For example, a rotor assembly coupler may include a bearing, bushing, or the like that mechanically engages a portion of a stator, such as by a press-fit, providing for both axial and radial retention of a rotor assembly within a stator of a rotary device as well as facilitating smooth rotational coupling of the components of a rotary device.

A surface of rotor assembly coupler 20 oriented toward the interior of the rotary device may be used to retain the slip ring elements 30 or other components of the rotor assembly on the rotor shaft 11. The surface of the rotor assembly coupler 20 oriented toward the interior of the rotary device may also include a feature or features that mechanically engage the adjacent slip ring elements or other rotor assembly components and prevents them from rotating about the rotor shaft 11 with respect to the rotor assembly coupler 20. This may include one or more surface projections or depressions configured to engage a complementary feature of the adjacent rotor assembly component.

The stator interface portion 21 and an attachment portion 23 of the rotor assembly coupler 20 may be supported about an axial hub of the rotor assembly coupler by two or more support arms extending radially outwardly from the axial hub of the rotor assembly coupler. Spaces between the axial hub, the support arms, and the outer circumference of the rotor assembly coupler that align with corresponding spaces in insulator discs or other components of the rotor assembly may permit routing of rotor assembly leads 37 from the slip ring elements 30 to the interior of the rotor assembly coupler 20. In various embodiments, the axial hub and support arms of a rotor assembly coupler may comprise the surface of the rotor assembly coupler oriented toward the interior of the rotary device or may be located near the interior end of the rotor assembly coupler.

A rotor assembly 10 in accordance with various embodiments includes a plurality of slip ring elements 30. In accordance with various embodiments and as illustrated in FIGS. 3-4D, each slip ring element 30 comprises a slip ring 31 and an insulator disc 32. In general, each slip ring 31 is a conductive, ring-shaped structure, and each insulator disc 32 is a substantially non-conductive, disc-shaped structure that provides support for a slip ring 31 with respect to the rotor shaft 11 and also provides for electrical isolation of adjacent slip rings 31 in the rotor assembly 10.

In accordance with various embodiments, each slip ring element of a rotary device may have substantially identical physical and electrical specifications. The modular nature of each slip ring element may facilitate assembly of rotary devices comprising a plurality of physically and electrically uniform slip ring elements, thereby providing for uniform and reliable mechanical and electrical performance of the rotary device.

In various alternative embodiments, a slip ring element may be individually provided with a particular component (i.e., a slip ring or insulator disc) or specification to produce a desired electrical performance for a particular slip ring connection within a rotary device. For example, a particular slip ring element may have a slip ring comprising a conductive material that differs from that of the slip rings of other slip ring elements of the device to provide for a particular electrical performance specification for the corresponding electrical connection. Alternatively, a particular slip ring element of a device may have a different physical specification such as an axial length of a slip ring portion, an insulator portion, or both, that spans multiple slide contact positions of a corresponding stator assembly. In accordance with various embodiments, the modular nature of the slip ring elements and the rotary devices comprising the slip ring elements may variously provide for improved uniformity or improved capacity for customization of a rotary device.

In various embodiments, the slip rings 31 of slip ring elements 30 are made of a metal or metal alloy, for example, copper, beryllium-copper, brass, or the like. The slip rings 31 may be further treated, for example, by coating with a precious metal such as gold to enhance the conductivity and/or electrical performance of the electrical connection between the slip ring and the slide contact of the stator assembly. Similarly, the slip rings 31 may be polished or otherwise provided with physical properties or specifications that may enhance the performance of a slip ring electrical connection, such as by providing for an enhanced signal to noise ratio. The slip rings may be manufactured, for example, by cutting rings of the desired width from metal tubing having the required material and dimensional specifications. In alternative embodiments, slip rings may be comprised of conductive polymers. In still other embodiments, slip rings may be manufactured of any material that may be provided with a conductive surface, such as by thin film metal deposition using any of a variety of chemical or physical deposition techniques. Any manner of manufacturing a slip ring from any material or combination of materials to produce a slip ring suitable for conducting electrical signal between a slide contact and a conductor electrically connected to the slip ring is within the scope of the present disclosure.

The insulator disc 32 of each slip ring element 30 is a generally disc-shaped structure that is substantially non-conductive. As used herein, the terms "substantially non-conductive," "insulative," "dielectric," and variations thereof may be used interchangeably to describe a material or structure that generally does not conduct an electrical current. A substantially non-conductive structure may be constructed of material that is non-conductive, or may be constructed of a conductive material such as a metal that is rendered substantially non-conductive by treatment of the material or structure, for example, by coating a conductive structure with a non-conductive material. Substantially non-conductive materials may include materials with high resistivity, such as glass, ceramics, polymers, plastics, composites, or the like.

An insulator disc 32 in accordance with various embodiments comprises a slip ring portion 33 with a first outer circumference and a spacer portion 34 with a second outer circumference that is greater than the first outer circumference. The circumferential edge of the insulator disc 32 in such an embodiment has a "stepped" appearance from a profile perspective (i.e., a two-level outer circumference profile) due to the different diameters of slip ring portion 33 and spacer portion 34 of the insulator disc. The insulator disc 32 may be substantially cylindrical in shape (i.e., generally having the shape of a right cylinder), for example, having a slip ring portion side (i.e., front face) and a spacer portion side (i.e., rear face) of the insulator disc that are both generally flat, with the exception of certain features that are described in greater detail herein. In alternative embodiments, the insulator discs may have shapes or profiles that depart from a generally cylindrical shape and may have, for example, a domed, conical, or irregular shape, while still having a substantially circular cross section coaxial to the rotor shaft 11 and a two-level outer circumference including a slip ring portion 33 and a spacer portion 34, as described above. Any of a variety of insulator disc shapes or profiles is possible and included within the scope of the present disclosure.

In various embodiments, the slip ring portion 33 and the spacer portion 34 of the insulator disc are radially supported about an axial hub 35 by two or more radial arms 36. Referring now to FIGS. 4A-4F, various views of a slip ring element 30 are shown, illustrating an insulator disc 32 having with three radial arms 36 extending from the hub 35 to the slip ring portion 33 and spacer portion 34. Spaces 40 between the hub 35, the radial arms 36, and the slip ring portion/spacer portion 33/34 permit rotor assembly leads 37 to be run from each slip ring 31 to the rotor assembly coupler 20, thereby facilitating electrical connection of each slip ring with the rotor assembly end of a rotary device. An opening at the axis of the hub 35 of each insulator disc 32 is configured to receive the rotor shaft 11.

An insulator disc 32 may further include various features that facilitate termination of a rotor assembly lead 37 and electrical connection of the rotor assembly lead to the slip ring 31 of each slip ring element 30. In various embodiments and as shown in FIG. 4F, an insulator disc 32 may include a channel 41 in the spacer portion-side surface (i.e., the rear face) of the insulator disc extending from a space 40 to a terminal penetration 42 through the spacer portion 34. A channel 41 may be of a suitable width, depth, and configuration to receive an insulated portion of a rotor assembly lead 37 and to mechanically retain the rotor assembly lead 37, such as by a press-fit interface (i.e., an interference fit or friction fit). A terminal penetration 42 through the spacer portion 34 is configured to permit an uninsulated terminal 38 of a rotor assembly lead 37 to pass through the spacer portion 34 of an insulator disc 32 and contact a slip ring 31. In an assembled slip ring element 30, the terminal 38 of the rotor assembly lead 37 is located between the first outer circumference of the slip ring portion 33 of the insulator disc 32 and the inner surface of the slip ring 31. An insulator disc may further include an arcuate deflection channel 43 located radially inward relative to the first outer circumference of the slip ring portion 33 and the terminal penetration 42. A deflection channel 43 permits the portion of the insulator disc located between the first outer circumference and the deflection channel 43 to elastically or resiliently flex or deflect to accommodate a terminal 38 of a rotor assembly lead 37 beneath a slip ring 31 while exerting sufficient constant pressure on the terminal 38 to maintain the terminal in fixed, electrical contact with the slip ring 31. Explained another way, the terminal 38 of a rotor assembly lead 37 is electrically connected to the slip ring 31 by a press-fit of the slip ring over the first outer circumference of the insulator disc, with the terminal 38 mechanically fixed between the slip ring and the insulator disc by compression of the terminal between the slip ring 31 and the first outer circumference of the insulator disc 32. In various embodiments, the first outer circumference of an insulator disc may further include a depressed region to accommodate a terminal 38 of a rotor assembly lead 37 beneath a slip ring 31.

Other features or configurations for mechanically fixing a terminal of a rotor assembly lead in electrical contact with a slip ring are possible in alternative embodiments. For example, the first outer circumference of an insulator disc may include an axial groove of suitable dimensions for receiving a terminal and maintaining it in electrical contact with a slip ring, rather than a deflection channel or a depressed region. In another example, an insulator disc may include channels, grooves, or penetrations that permit routing of the terminal of a rotor assembly lead transverse to the axis of the rotor assembly (i.e., parallel to or concentric with the circumference of the slip ring). Any configuration of an insulator disc that permits routing and securing of a portion of a rotor assembly lead and/or terminal with respect to the insulator disc and slip ring and that places the terminal in electrical contact with the slip ring is within the scope of the present disclosure.

Insulator discs may also include structures or features that permit an insulator disc to operatively engage an adjacent surface. In accordance with various embodiments and as illustrated in FIGS. 4A-4D, an insulator disc may have projections 44 extending from a face of the insulator disc such as the front face of an insulator disc 32. The projections 44 may be configured to engage an adjacent component of the rotor assembly by fitting within corresponding recesses 45 in the adjacent component, such as the rear face of another insulator disc 32 or a surface of the rotor assembly coupler. For example, the projections 44 and corresponding recesses may interface by a press-fit or a snap-fit connection. Projections 44 and corresponding recesses in an adjacent component may be configured such that an insulator disc 32 is torsionally fixed with respect to the adjacent component. In this manner, a plurality of slip ring elements may be assembled to form a substantially torsionally fixed rotor assembly.

In various embodiments, insulator discs may be formed or manufactured with a unitary construction. For example, insulator discs may be molded from a non-conductive thermoplastic resin. In alternative embodiments, each insulator disc may be comprised of multiple, separate components that are joined to form an insulator disc. For example, each insulator disc may be comprised of a slip ring portion that is separate from the spacer portion. In such an embodiment, separate components of an insulator disc may be permanently joined, or may be modularly assembled using features such as the projections and recesses described above.

Slip ring elements are assembled into a rotor assembly 10 by sliding the slip ring elements 30 onto a rotor shaft 11. In the embodiments illustrated in FIGS. 3-4D, each hub 35 has a circular opening at its axis, and the rotor shaft 11 has a circular cross section. The opening at the axis of each hub 35 may be sized such that the opening is complementary to the diameter of rotor shaft 11 and the insulator discs slide on freely (i.e., a loose or light interference fit). In other embodiments, the opening may be undersized with respect to the diameter of rotor shaft 11, such that the insulator discs 32 are press-fit onto the rotor shaft 11 to provide an interference fit with a suitable strength of fit to provide resistance to axial and torsional movement of the insulator disc relative to the rotor shaft following installation of the insulator disc on the rotor shaft. In yet other embodiments, the hub of an insulator disc and the rotor shaft may have other cross sectional profiles, such as parallel keyed configurations or the like, that provide a hub joint with resistance to torsional movement of an insulator disc about the rotor shaft while still permitting modular assembly of slip ring elements on the rotor shaft.

In various embodiments, the axial lengths of the slip ring elements or portions thereof in a rotor assembly may vary. For example, the rotary devices 100A and 100B illustrated in FIGS. 1A-2B each comprise 34 uniform slip ring connections. However, a rotary device including various components of the illustrated devices, such as a stator 51, a rotor shaft 11 and rotor assembly coupler 20, and housing components, may be configured to have a variety of numbers and configurations of electrical connections by varying the configuration of the slip ring elements and the slide contacts.

Figure 4B:
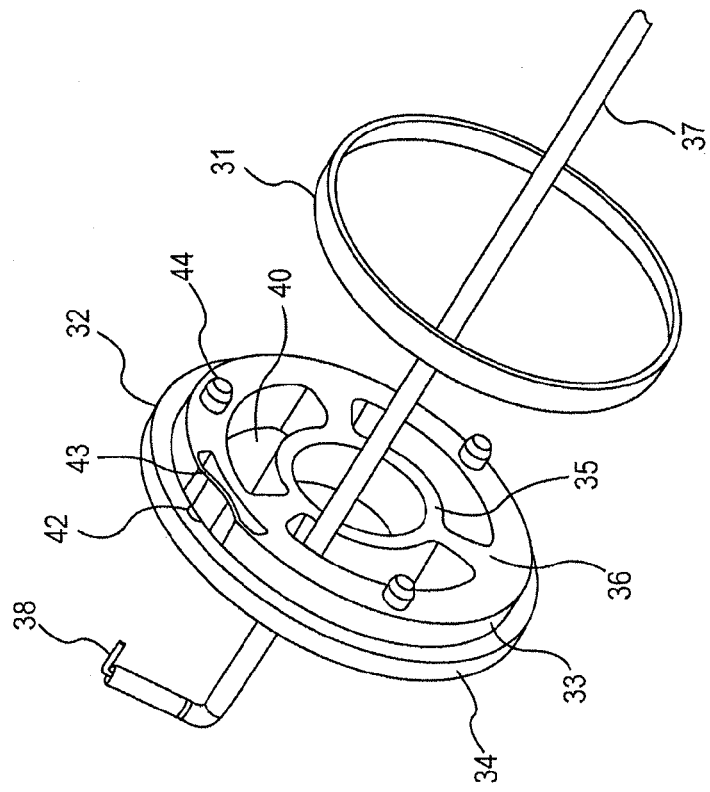
FIG. 4B is an exploded view of a front face of a slip ring element showing a terminated rotor assembly lead in accordance with various embodiments.
Figure 4A:
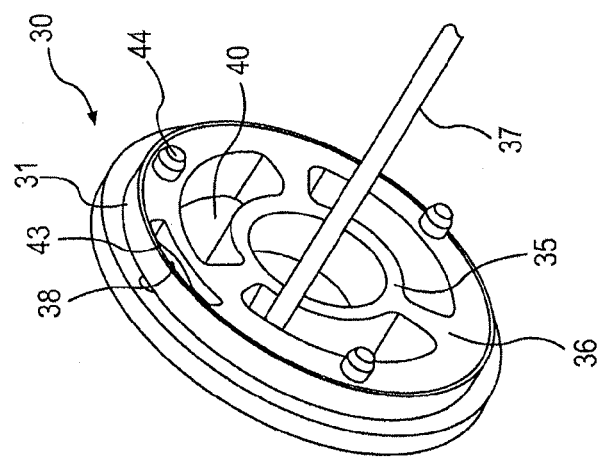
FIG. 4A is a perspective view of a front face of a slip ring element and a rotor assembly lead in accordance with various embodiments.
Figure 4D:
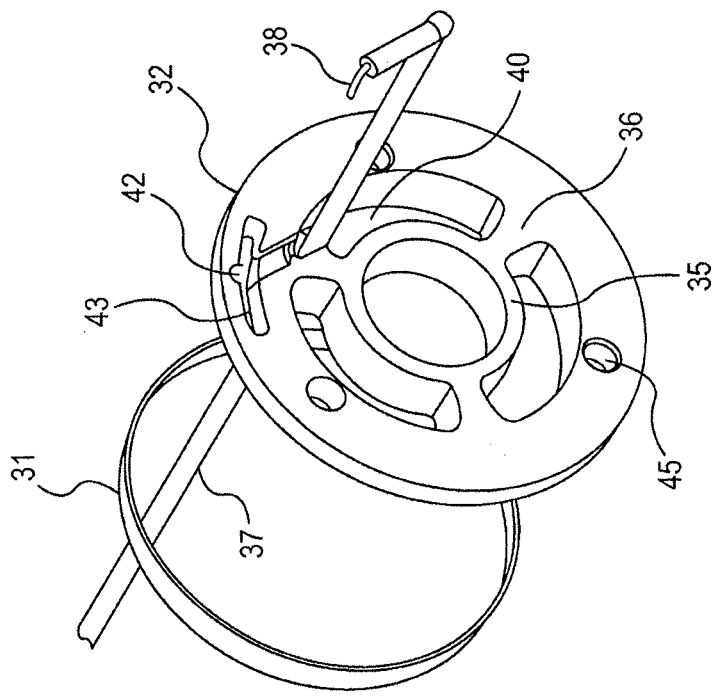
FIG. 4D is an exploded view of a rear face of a slip ring element showing a terminated rotor assembly lead in accordance with various embodiments.
Figure 4C:
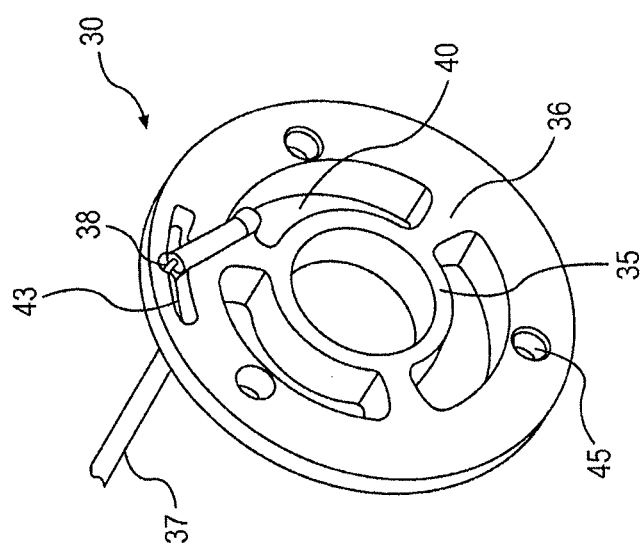
FIG. 4C is a perspective view of a rear face of a slip ring element showing a terminated rotor assembly lead in accordance with various embodiments.
Figure 4F:
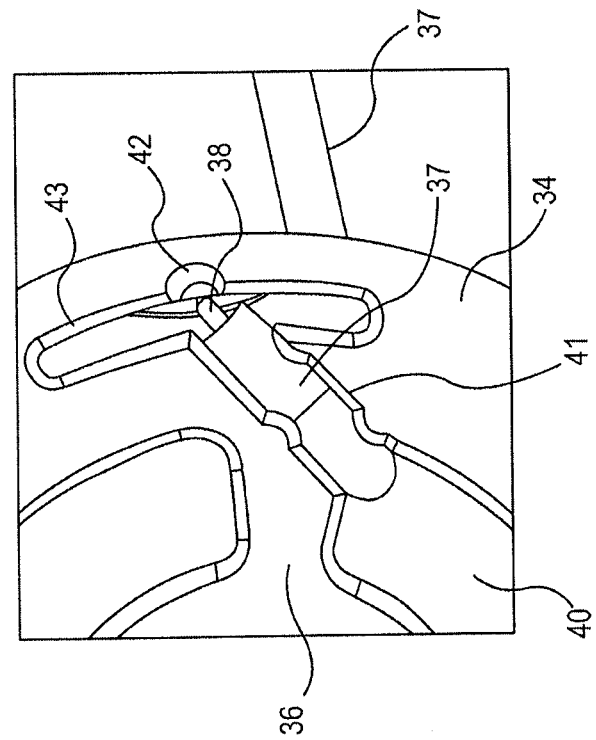
FIG. 4F is a magnified view of a rear face of a slip ring element showing a terminated rotor assembly lead in accordance with various embodiments.
Figure 4E:
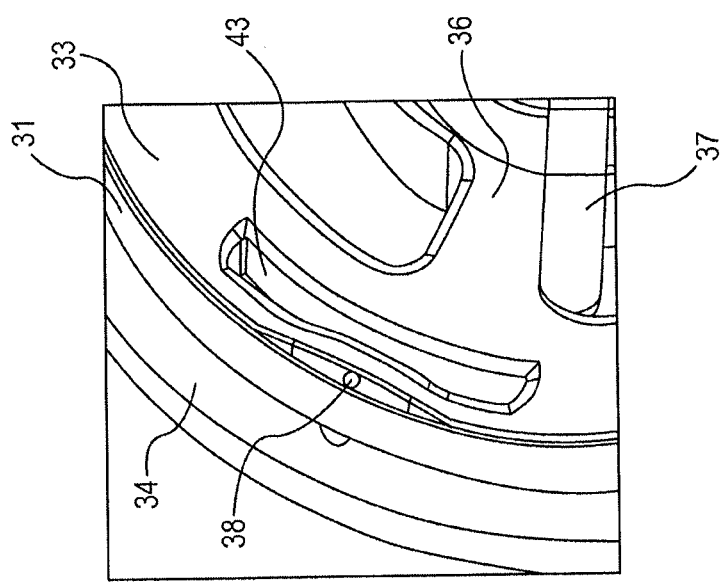
FIG. 4E is a magnified view of a front face of a slip ring element showing a terminated rotor assembly lead in accordance with various embodiments.

For example, and with reference to FIG. 4A, insulator discs with varying axial lengths (i.e., thicknesses) of the spacer portion 34 may be used to provide the necessary electrical resistance between adjacent slip rings 31. Varying axial lengths of a spacer portion 34 of a slip ring element 30 may be produced by using multi-component insulator discs having multiple, separate spacer portions, or by using insulator discs having a unitary construction and a range of available sizes with respect to the axial length of the spacer portion 34.

Similarly, insulator discs with varying axial lengths of the slip ring portion 33 may be used in a rotor assembly. For example, an insulator disc with an extended slip ring portion 33 may be provided to accommodate longer slip rings 31 that could be used to make electrical contact with more than one slide contact to accommodate greater electrical current through the slip ring. Varying axial lengths of a slip ring portion 33 of a slip ring element 30 may be produced in a manner similar to that described above with respect to the spacer portion. For example, an elongated slip ring portion of a slip ring element may comprise three separate slip ring portion components, each separately sliding on to rotor shaft 11 and each receiving a rotor assembly lead 37, with an elongated slip ring fitting over the three slip ring portion components and rotor assembly leads and making contact with as many as three rotor assembly lead terminals 38 in this example. In this manner, a rotor assembly of the present disclosure may be modularly or scalably configured, and a rotary device having a variety of electrical connection configurations may be achieved using various combinations of components that can be modularly assembled.

A rotary device in accordance with various embodiments of the present disclosure and as illustrated in FIGS. 1A-2B includes a stator assembly 50. The stator assembly 50 may comprise a stator 51, a plurality of slide contacts 52, and a plurality of stator assembly leads 53. In accordance with various embodiments, stator 51 is cylindrically shaped and defines a cavity configured to receive a rotor assembly 10.

In various embodiments, the stator 51 of a stator assembly 50 is substantially non-conductive. A stator 51 may be formed or machined from any of a variety of suitable materials, including both conductive and non-conductive materials, for example, metals or metal alloys, ceramics, or plastics. A stator 51 constructed from a conductive material may be rendered substantially non-conductive by coating or otherwise treating it with a non-conductive material.

A stator 51 may have various features to facilitate operative connection of the rotor shaft 11. For example, the cavity of a stator 51 may include a bearing configured to receive an end of a rotor shaft 11 and provide for rotation of the rotor assembly 10 within the stator 51. The interior surface of the cavity of the stator 51 may also have dimensions or features that permit operational engagement of rotor assembly 10. For example, the cavity of stator 51 may be configured to receive a bearing or bearings located at one or both ends of the rotor assembly 10, such as by a press-fit connection, thereby providing for axial and radial retention of the rotor assembly 10, with the bearing or bearings providing for rotation of the rotor assembly within the stator. Likewise, the interior surface of the cavity of a stator may be configured to engage one or more o-rings or other gaskets, seals, or packings such that the interior of the rotary device is protected from external fluids or contaminants throughout dynamic interaction (i.e., rotation) of the rotor assembly with respect to the stator. Alternatively, the interior surface of the cavity of a stator may be configured o-rings or other seals. Any of a variety of configurations of a stator and a rotor assembly that facilitate retention and rotation of the rotor assembly 10 within the stator 51, along with sealing of the slip ring connections within the rotary device and protection of the slip ring connections from environmental conditions external to the rotary device, are within the scope of the present disclosure.

Figure 7:
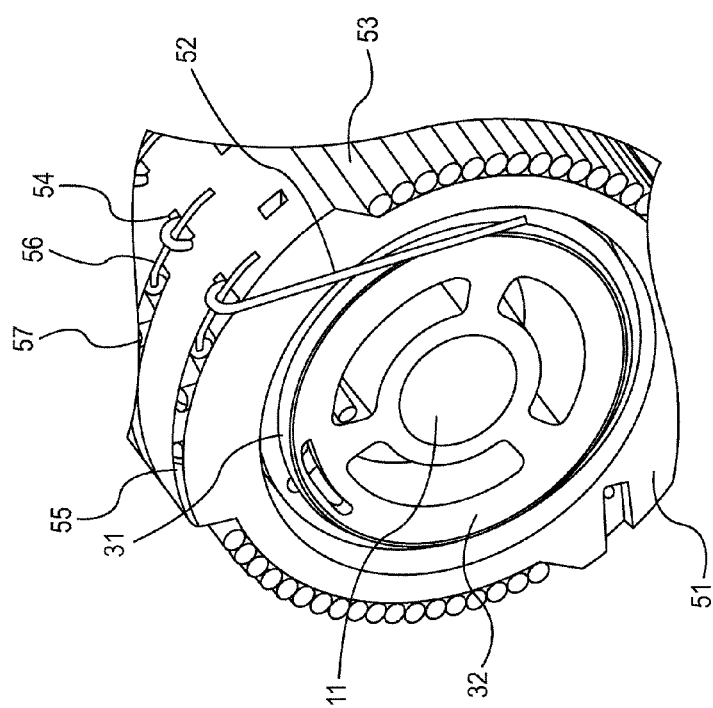
FIG. 7 is a cut-away perspective view of a rotor assembly and stator assembly of a partially assembled rotary device showing a contact between a slide contact and a slip ring in accordance with various embodiments.
Figure 8:
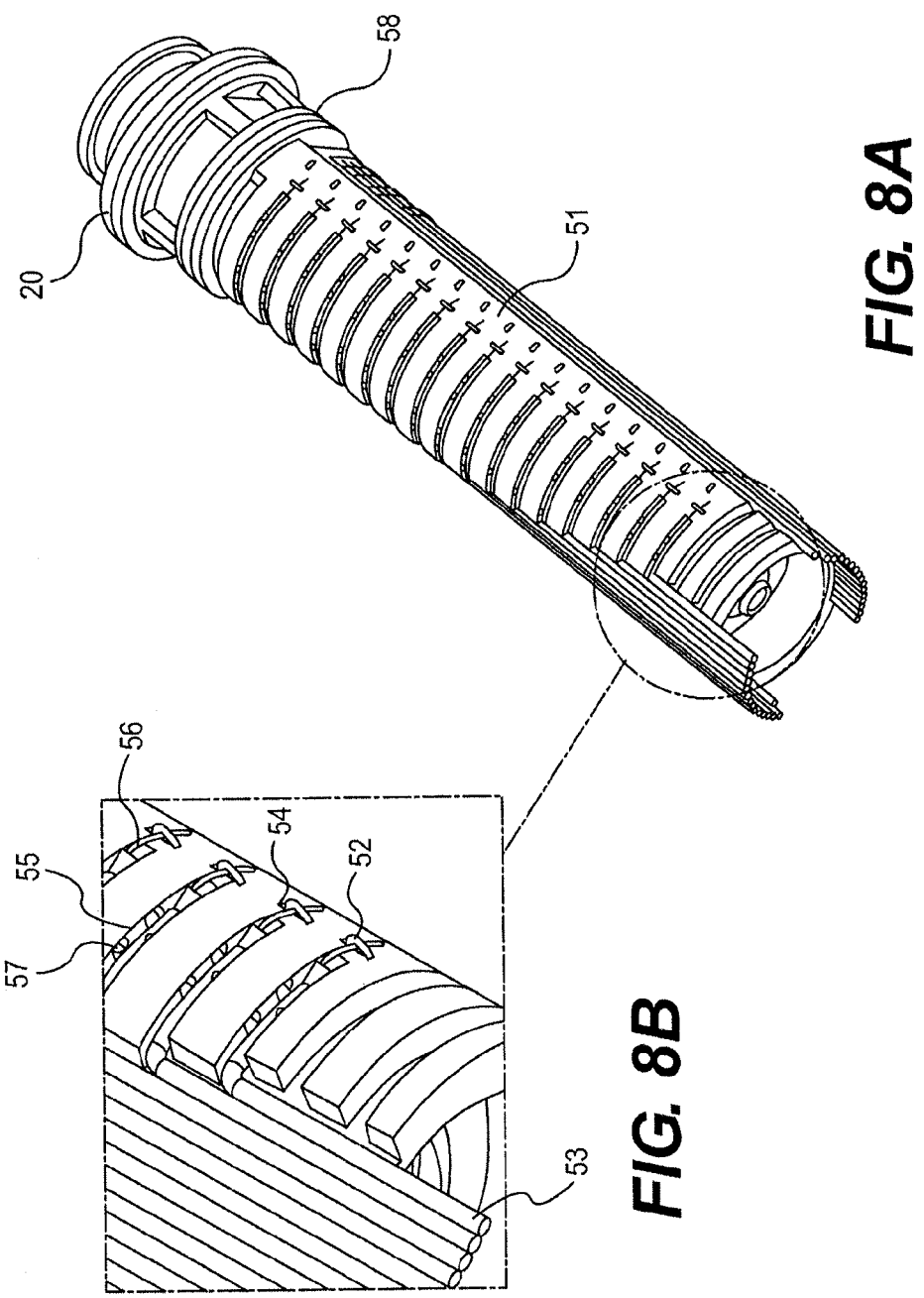
FIG. 8A is a perspective view of a stator assembly with a rotor assembly inserted in accordance with various embodiments.
FIG. 8B is a magnified view of FIG. 8A.

A stator 51 also includes features for electrically connecting components of the stator assembly 50 to the slip rings 31 of each slip ring element in the rotor assembly. With reference now also to FIGS. 7 and 8, a stator 51 may include slide contact penetrations 54 for insertion of each slide contact 52. A stator 51 may also include grooves or channels 55 along the exterior surface of the stator for routing of the stator assembly leads 53 from the end of the stator to each slide contact 52 and for mechanically and electrically connecting a stator lead terminal 56 of each stator assembly lead 53 to each slide contact 52. Similarly, portions of the exterior surface of a stator 51 may be configured with a relieved region or a decreased diameter to accommodate parallel routing of a plurality of stator assembly leads 53 within a stator housing 61.

The channels 55 in a stator 51 may be oriented along circumferential arcs of the outer surface of the stator and provide for retention of the stator assembly leads 53 and alignment of the stator lead terminals 56 with the slide contacts 52 and with the slip rings 31 of the rotor assembly 10. In the embodiment shown in FIG. 8, the lengths of the channels 55 are progressively longer from the stator end of the stator 51 to the rotor end by a distance approximately equal to the distance between every other slip ring of the rotor assembly. Such a configuration permits orderly parallel routing of stator assembly leads that terminate at a row of slide contacts running parallel to the axis of the rotary device.

Figure 5:
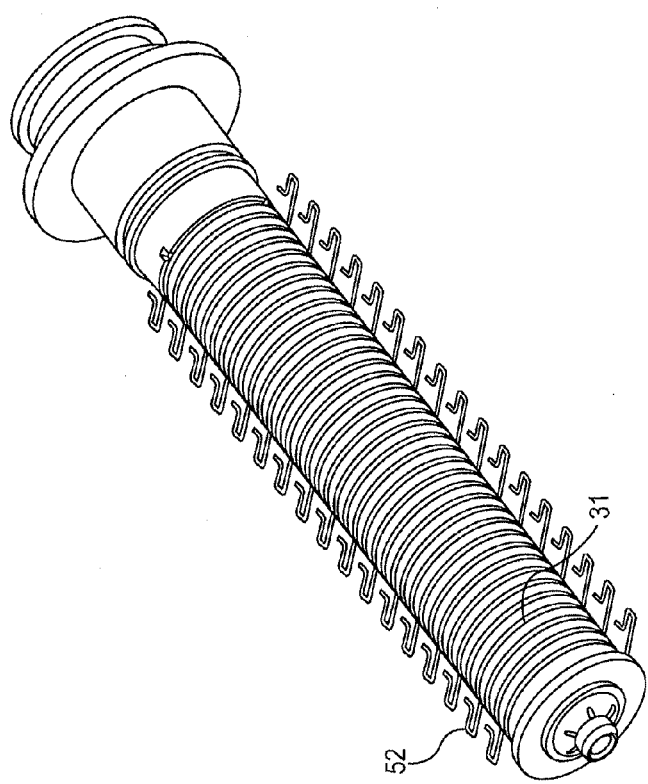
FIG. 5 is a perspective view of a rotor assembly also showing positions of corresponding slide contacts from a stator assembly in accordance with various embodiments.
Figure 6B:
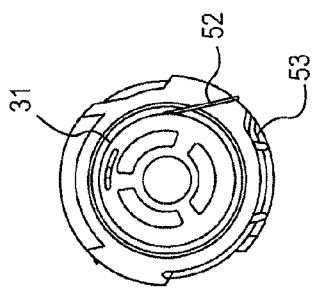
FIG. 6B is a cross section view of a partially assembled rotary device in accordance with various embodiments showing a terminated stator assembly lead and the position and orientation of a slide contact aligned with an odd-numbered slip ring element of the device.
Figure 6D:
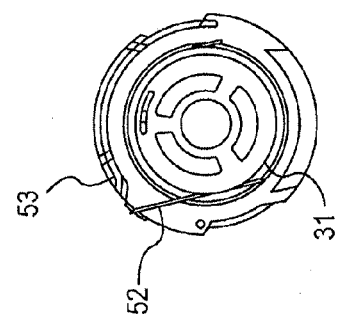
FIG. 6D is a cross section view of a partially assembled rotary device in accordance with various embodiments showing a terminated stator assembly lead and the position and orientation of a slide contact aligned with an even-numbered slip ring element of the device.
Figure 6A:
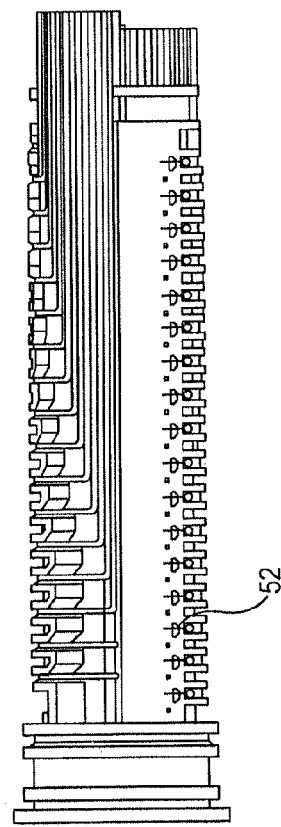
FIG. 6A is a top view of a partially assembled rotary device in accordance with various embodiments showing a row of slide contacts and terminated stator assembly leads aligned with odd-numbered slip ring elements of the device.
Figure 6C:
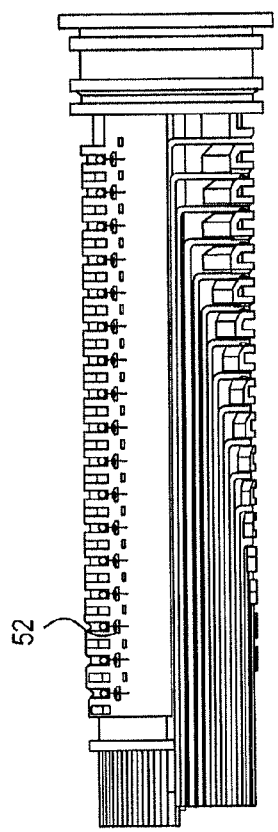
FIG. 6C is a bottom view of a partially assembled rotary device in accordance with various embodiments showing a row of slide contacts and terminated stator assembly leads aligned with even-numbered slip ring elements of the device.

The stator assemblies 50 illustrated in FIGS. 1B and 2B each include two rows of slide contacts oriented substantially perpendicularly to the axis of the rotary device and on opposite sides of stator 51, with the slide contacts 52 in each row aligning with every other slip ring 31 in the rotor assembly 10. This arrangement of the slide contacts 52 with respect to the slip ring elements of a rotor assembly in accordance with various embodiments is illustrated in greater detail in FIGS. 5-6D. FIG. 5 shows a perspective view of a rotor assembly in accordance with various embodiments and the relative positions of slide contacts 52 arranged in two rows on opposite sides of the rotor assembly with the stator removed for purposes of illustration. FIGS. 6A-6D illustrate a partially assembled rotary device in accordance with various embodiments showing two rows of slide contacts 52 on opposite sides of the stator, with the top view (FIG. 6A) showing slide contacts aligned with odd-numbered slip ring element positions and the bottom view (FIG. 6C) showing slide contacts aligned with even-numbered slip ring element positions of the rotary device. FIGS. 6B and 6D illustrate representative cross-section views of a rotary device at an odd-numbered slip ring element position and an even-numbered slip ring element position, respectively, to show the relative position and orientation of a slide contact 52 and a slip ring 31. Such an even radial and axial distribution of slide contacts within a rotary device may provide for a symmetrical or balanced distribution of frictional and/or pressure forces between the stator assembly and the rotor assembly. However, stators having any number of rows of slide contacts distributed symmetrically or asymmetrically about the circumference of the stator and having slide contacts aligned with slip rings in any possible sequence are within the scope of the present disclosure. Likewise, stators having slide contacts arranged in other patterns, such as spirals or other non-linear patterns, are also within the scope of the present disclosure.

Referring again to FIGS. 7-8, a portion of each stator assembly lead 53 adjacent to the stator lead terminal 56 of the lead and fitting in channel 55 may be mechanically fixed in the channel 55 using an interference fit such as a series of alternating projections 57 in the side wall of each channel. The stator lead terminal 56 of each stator assembly lead 53 may be likewise mechanically secured by and electrically connected to a slide contact 52 by insertion of the slide contact into a slide contact penetration 54 in the wall of the stator 51. A fixed end of each slide contact is press-fit into a slide contact penetration 54 and retained in position by an interference fit. The fixed end of each slide contact 52 retains the stator lead terminal 56 between a bend or curve of the fixed end of the slide contact and a portion of the exterior surface of the stator. In other embodiments, each stator lead terminal 56 may further be press-fit into a channel approximating the size of the terminal.

A free end of each slide contact 52 extends into the cavity of stator 51 and makes contact with a slip ring 31, as shown in FIG. 7. The slide contacts 52 may be biased to maintain mechanical contact and an electrical connection with the slip rings 31 by the orientation of the slide contact penetrations 54 and/or the configuration of the slide contacts 52. For example, the slide contacts 52 may be configured so that they are resiliently biased toward the slip rings 31 after installation in the stator 51. The slide contacts are constructed of a conductive material and may be formed, for example, of a wire bent or formed to a suitable configuration or by cutting, stamping, or etching from a sheet of material. The free end of each slide contact 52 may be substantially straight, contacting a slip ring tangentially as illustrated in FIG. 7, or the free end of each slide contact may have an arc or bend that corresponds to a portion of the circumference of a slip ring and increases the contact area between the slip ring and the slide contact.

A rotary device in accordance with various embodiments includes a housing configured to cover or encase the device. A housing may be configured to protect the rotary device and the electrical connections therein from the external environment. A housing is generally non-conductive, and may be constructed of a material that is substantially non-conductive or may be constructed of a conductive material that is treated to render the housing substantially non-conductive. Referring again to FIGS. 1A-2B, a housing may be comprised of one or more components, such as a stator housing 61 and/or a rotor assembly coupler overmold 62. In alternative embodiments, a portion of a rotary device or rotary device component, such as a portion of an external surface of a rotor assembly coupler, may comprise a portion of the external surface of the finished device without being further covered by or encased in a housing component such as a rotor assembly coupler overmold.

In various embodiments, a stator housing 61 may be constructed as a unitary piece, as illustrated in FIGS. 1A and 1B, and configured to receive a stator assembly 50 and to retain the stator assembly by a threaded connection, press-fit, snap-fit, or other interference fitting of the stator housing over the stator assembly. In other embodiments and as illustrated in FIGS. 2A and 2B, a stator housing 61 may comprise multiple pieces that are fit together over a stator assembly 50 and joined by any of a variety of suitable means, such as by a snap-fit, adhesive connection, welded connection, or the like. The stator 51 and/or stator housing 61 may further include one or more o-rings 58 or other gaskets, seals, or packings to provide a seal between the stator assembly and the stator housing at one or both ends of the stator and to prevent external fluids or other contaminants from contacting the stator assembly. In various embodiments, a stator housing 61 may also provide for further retention of the slide contacts 52 in the slide contact penetrations 54 of the stator and help to maintain mechanical and electrical contact of the fixed end of the slide contacts with the stator lead terminals 56.

Similarly, rotor assembly coupler 20 of rotor assembly 10 may be encased by a rotor assembly coupler overmold 62. A rotor assembly coupler overmold 62 may be configured and attached to the rotor assembly coupler 20 or to the attachment portion 23 of a rotor assembly coupler in a manner similar to that described above for a stator housing 61.

A stator housing 61 may be configured for attachment to a sheath, housing, or other external protective covering of a multi-conductor electrical cable. For example, and as illustrated in the cable-to-cable rotary device 100A shown in FIGS. 1A and 1B, a stator housing 61 may terminate in a male press-fit cable sheath connection 63 resembling a hose barb fitting over which a cable sheath (not shown) may be fit to provide a sealed connection between the rotary device 100A and an electrical cable to a remote device. Likewise, the rotor assembly coupler overmold 62, rotor assembly coupler 20, or attachment portion 23 of a rotor assembly coupler may be similarly configured to accept an electrical cable sheath (not shown). In the illustrated rotary device 100A, rotor assembly coupler 20 is configured to receive a cable within the cavity of the rotor assembly coupler.

In cable-to-cable rotary device embodiments, wire leads from the rotary device extend outward from the device to remote devices, connectors, or other components. For example, rotor assembly wire leads 37 may extend outwardly from the rotor end of the cable-to-cable rotary device 100A through an attached cable sheath (not shown) to a first remote electronic device. Likewise, stator assembly leads 53 may extend outwardly from the stator assembly end of the rotary device 100A through an attached cable sheath (not shown) to a second remote electronic device. In this manner, rotary device 100A can permit a first remote electronic device and a second remote electronic device to be rotated freely with respect to one another without twisting or binding of the of the connecting cable while maintaining a continuous electrical connection across multiple electrical channels.

In various embodiments, a rotary device may include connectors (i.e., male plug connectors, female socket or receptacle connectors, or any type of device for providing an interface between electrical circuits using a mechanical assembly) at one or both ends of the rotary device for making electrical connections between the rotary device and remote electrical devices. For example, and as illustrated in FIGS. 2A and 2B, a connector-to-connector rotary device 100B may comprise a male plug connector 71 on the stator end of the rotary device and a female connector 72 on the rotor end of the rotary device. The connectors may be configured to support multiple discrete electrical channels that may be electrically connected to the rotor assembly leads (not shown) for a connector at the rotor end or to the stator assembly leads 53 at the stator end. In accordance with various embodiments, connectors may be selected or configured to provide for resistance to entry of fluid or other external contaminants and be suitable for use, for example, intraluminally or intravascularly. A first remote electronic device may be connected to the male plug connector 71 of rotary device 100B, and a second remote electronic device may be connected to the female connector 72 using corresponding mateable connectors. In this manner, rotary device 100B can permit a first remote electronic device and a second remote electronic device to be rotated freely with respect to one another without twisting or binding of the of the connecting cable while maintaining a continuous electrical connection across multiple channels.

In accordance with various embodiments, any type of connector that permits parallel conduction of separate electrical channels through the connector, such as a multi-pin connector, may be used. A wide variety of connectors are known to persons of ordinary skill in the art, including such connectors as are described and illustrated in U.S. Pat. Nos. 7,326,091, 7,661,995, 7,938,670, D596,127, D615,932, and D616,825, which patents are hereby incorporated by reference in their entireties. Likewise, the illustrated rotary device configuration shown in FIGS. 1B and 2B having a male plug connector at one end and a female connector at the other end of the rotary device is for purposes of illustration only. In accordance with various embodiments, any type of connector or combination of connectors may be used at the ends of a rotary device without limitation to any particular combination of connector gender or type. Likewise, a rotary device may have a connector at one end and a cable connection at the other end. Rotary devices having any of the range of possible permutations of the various end configurations described above are within the scope of the present disclosure.

In a rotary device comprising one or more connectors, either the rotor assembly leads 37, or the stator assembly leads 53, or both, may terminate at and electrically connect to the connectors at the respective ends of the device in any suitable manner. Likewise, the connectors may be connected to the rotor assembly coupler 20 or the end of the stator 51 opposite the rotor assembly coupler 20 using any suitable means, for example, a press-fit, threaded fit, bayonet connector, or any other interference, welded, brazed, or adhesive fit. The interface between the stator 51 or rotor assembly coupler 20 and a connector may be configured such that mechanical attachment of the connector simultaneously provides for electrical connection of the stator assembly leads 53 or the rotor assembly leads 37 to the attached connector.

In other embodiments, electrical connection of the leads to a connector may be made separately from attachment of the connector to the stator assembly end or rotor assembly coupler using any suitable means, either before or after attachment of the connector to the stator assembly end or the rotor assembly coupler.

In accordance with various embodiments, a rotary device may be suitable for use in a medical device. For example, a rotary device as disclosed herein may be used to electrically connect a first remote electronic device that may deployed in the body of a human patient to a second remote electronic device that may remain outside of the body of the human patient. Various medical devices, such as an electronic instrument, apparatus, or implant deployed within a body lumen or cavity may require rotation during insertion or operation while attached to an external electronic device such as a power source, monitor, data recorder, or computer by an electrical cable. In such a scenario, the ability to freely rotate the first remote electronic device while continuously maintaining an electrical connection with the external electronic device and without twisting, kinking, binding or jamming of the connecting electrical cable due to rotation of the first electronic device during a medical procedure is desirable.

Rotary devices in accordance with various embodiments disclosed herein may be suitable for use in medical facility such as a hospital or operating room or other patient care or diagnostic facility. For example, a rotary device may be compatible with the electronic performance requirements of any type of electronic device, including any type of medical electronic device, with respect to specifications such as current, voltage, impedance, and signal to noise ratio. A rotary device in accordance with various embodiments may be configured with components having specifications suitable for low voltage/low amperage current and signal transmission with low noise and high signal quality. Similarly, a rotary device may provide the physical performance specifications required in various medical settings, including, for example, resistance to entry of water or other fluids and the ability to meet regulatory requirements for single use and/or reusable devices with regard to cleanliness or sterilization. The rotary devices disclosed herein may also provide an ability to meet other physical requirements associated with medical device applications such small size and biocompatibility.

In accordance with various embodiments, a method of assembling a customized rotary device based on the electrical connection requirements of the components to be connected is provided. A method of assembling a customized rotary device may comprise steps of determining the number of electrical channels required by the components to be connected, as well as determining the electrical specification requirements for each channel. A method may further include selecting a rotor and stator assembly of the appropriate size, including the appropriate length and diameter. Likewise, the method may comprise selecting a rotor and stator assembly having the desired ends, such as cable ends or connector ends, based on the manner in which the rotary device will be attached to the remote components of the system. The connector ends or cables may be attached to the rotor and stator as described above. A method may further comprise attaching connectors to the electrical cables of the components to be connected, wherein the connectors correspond to or are compatible with connectors of the rotary device or connectors that may be located at the remote ends of cables extending from the rotary device.

Figure 9:
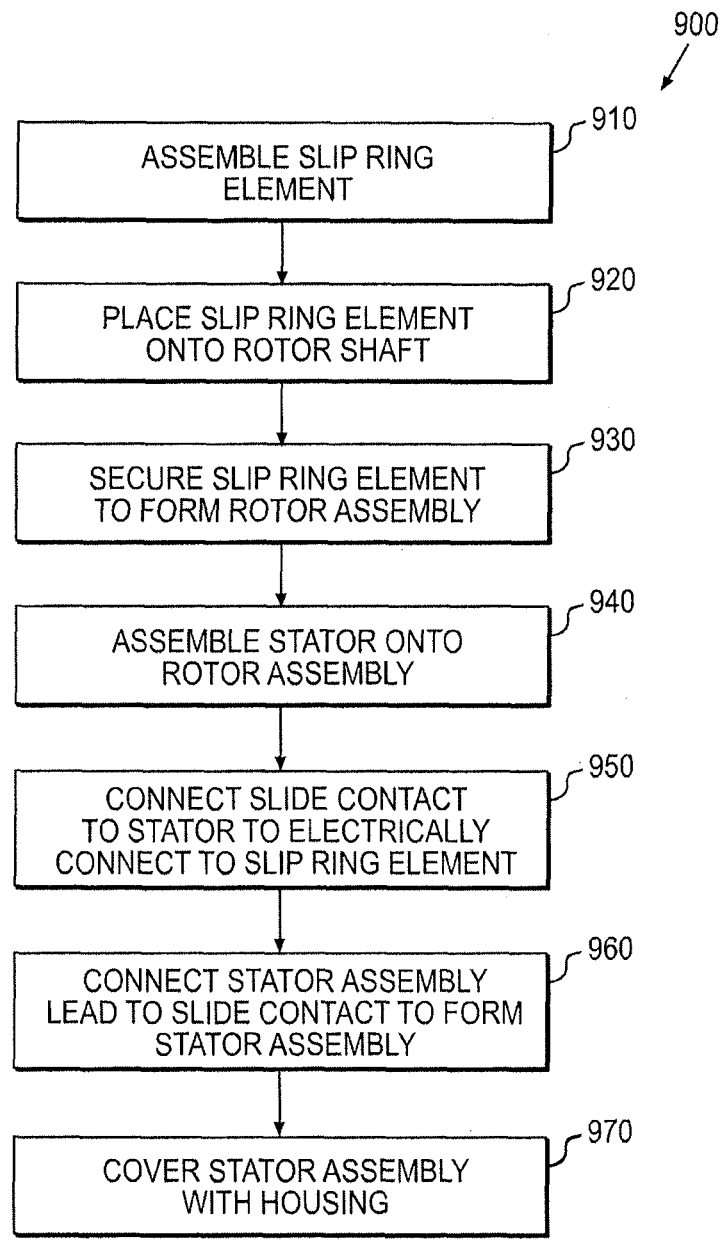
FIG. 9 is a flowchart of a fabrication process in accordance with various embodiments.

Following determination of the number of electrical channels and selection of the rotor assembly and stator assembly components, the rotor assembly may be assembled. FIG. 9 presents a flowchart 900 of a method of assembling a rotary device, such as the rotary devices 100A and 100B. At 910, slip ring elements are assembled, such as the slip ring 31. At 920, slip ring elements are placed onto a rotor shaft, such as the rotor shaft 11. Slip ring elements may be added to the rotor shaft and connected to a rotor assembly lead as disclosed herein. The number and configuration of the slip ring elements, including the axial length (i.e., thickness) of the spacer portion and/or the axial length of the slip ring may be varied or selected based on the electrical performance requirements of the system connected by the rotary device. For example, an insulator disc with an increased axial length of the spacer portion may be selected to provide greater isolation of adjacent slip rings that may carry greater current or power. Similarly, longer slip rings may be selected and installed in connection to multiple rotor assembly leads and making contact with multiple slide contact such that the same electrical signal is carried by multiple parallel leads in the connected system. At 930, slip ring elements are secured to form a rotor assembly, such as the rotor assembly 10. As each slip ring element is added, rotor assembly leads are routed through the spaces in the insulator discs and the terminals are connected to the insulator disc and the slip rings as described above. Portions of the length of the rotor assembly that are not required for making an electrical connection may be occupied by installing a spacer element of the appropriate length on the rotor assembly.

Following assembly of the rotor assembly, a stator, such as the stator 51, is assembled. At 940, the stator is assembled onto the rotor assembly. At 950, slide contacts, such as the slide contacts 52, are connected to the stator to electrically connect to the slip ring elements. At 960, stator assembly leads, such as the stator assembly leads 53, are connected to the slide contacts to form the stator assembly, such as the stator assembly 50. Stator assembly leads are routed along the outer portion of the stator and fixed in channels, and slide contacts are inserted into slide contact penetrations to mechanically secure and electrically connect the stator assembly lead terminals to the slide contacts. Slide contacts are inserted in positions in the stator corresponding to the appropriate slip rings of the rotor assembly and in the desired row, for example, to maintain a symmetrically balanced distribution of slide contacts about the rotor assembly.

At 970, the stator assembly is covered with a housing or overmold, such as the overmold 62. Following insertion of the slide contacts and routing and connection of the stator assembly leads, the stator housing and the rotor assembly coupler overmold may be attached to the rotary device. In various embodiments, the assembled rotary device may be packaged and sold in various configurations of cable-to-cable rotary devices, connector-to-connector rotary devices, or connector-to-cable rotary devices for installation in an electronic system by an end user or third party. In other embodiments, a rotary device may be connected to or installed in an electronic system, for example, by the rotary device manufacturer or assembler.

Rotary devices in accordance with various embodiments as described herein and methods of assembling the same may provide various benefits such as modularity and scalability that facilitate their application or use in a variety of systems and environments, as well as providing further benefits such as improved simplicity, reliability, and ease of manufacturing and assembly with respect to prior art devices and methods.

As used herein, the terms "rotor" and "stator" are applied for the sake of clarity and convenience with respect to components of the rotary devices described herein that are coupled in a rotationally operative manner. The term "stator" as used in the present disclosure is not limited to a fixed or non-moving portion of a rotary device. Rather, both the stator assembly and the rotor assembly of a rotary device as disclosed herein may rotate with respect to an external point of reference as well as with respect to each other.

As used herein, the term "remote" is used to refer to a device or connection that is located external to a rotary device at any distance from a rotary device.

Although the various rotary devices illustrated and described herein are shown as having various combinations of cable ends, male connector ends, or female connector ends, rotary devices having any suitable combination of cable and/or connector end, along with any combination of type or gender of connector end, are within the scope of the present disclosure. Likewise, the embodiments illustrated herein depicting rotary devices having a particular number of uniform slip ring electrical connections are for purposes of illustration only, and alternative embodiments utilizing greater or fewer slip ring connections or non-uniform slip ring connections are within the scope of the present disclosure.

Various embodiments of the invention have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. A rotary device comprising:
    a rotor shaft configured to rotate around a longitudinal axis;
    a plurality of rotor leads;
    a plurality of slip rings positioned on the rotor shaft, positioned axially adjacent to each other and configured to rotate around the longitudinal axis with the rotor shaft, each of the plurality of slip rings being electrically coupled to at least one of the plurality of rotor leads;
    a stator having one or more grooves or channels and defining a cavity that is configured to receive the rotor shaft and the plurality of slip rings;
    a plurality of stator leads; and
    a plurality of slide contacts coupled to the stator, the plurality of slide contacts being electrically coupled to at least one of the plurality of stator leads and at least one of the plurality of slip rings at any position relative to the rotor shaft and the plurality of slip rings, the at least one of the plurality of stator leads being routed along the one or more grooves or channels to electrically connect to at least one of the plurality of slide contacts.

2. The rotary device of claim 1 further comprising a plurality of insulator discs each including a slip ring portion configured to receive a respective slip ring of the plurality of slip rings and a spacer portion.

3. The rotary device of claim 2 wherein the spacer portion has a greater circumference than the slip ring portion.

4. The rotary device of claim 3 wherein each of the plurality of insulator discs includes a hub configured to receive the rotor shaft and at least two support arms connecting the hub to the slip ring portion and the spacer portion.

5. The rotary device of claim 4 wherein at least one channel is defined by each of the plurality of insulator discs between the hub, at least one of the at least two support arms, the spacer portion and the slip ring portion such that at least one of the plurality of rotor leads extends axially through the at least one channel.

6. The rotary device of claim 1 further comprising a rotor device coupler and a housing configured to cover the rotary device and including a stator housing and a rotor device coupler overmold.

7. The rotary device of claim 1 wherein each of the plurality of slide contacts is electrically coupled to the at least one of the plurality of stator leads by a press-fit connection.

8. The rotary device of claim 1 wherein each of the plurality of slide contacts are coupled to the stator by a press-fit connection.

9. The rotary device of claim 1 wherein the one or more grooves are circumferential and each axially align with at least one of the plurality of slip rings such that each of the plurality of stator leads extends axially along the stator and circumferentially along at least one of the plurality of circumferential grooves.

10. The rotary device of claim 1 wherein the stator defines a plurality of slide contact penetrations each axially aligned with one of the plurality of slip rings such that each of the plurality of slide contacts is electrically connected to the at least one of the plurality of stator leads at a location radially outward from the stator, extends radially inward through one of the plurality of slide contact penetrations and contacts one of the plurality of slip rings.

11. A rotary device comprising:
a rotor device configured to rotate around a longitudinal axis and including a rotor shaft, a first outer conductive surface and a second outer conductive surface;
a plurality of slip rings positioned on the rotor shaft;
a first rotor lead electrically connected to the first outer conductive surface and a second rotor lead electrically connected to the second outer conductive surface;
a stator device rotatably coupled to the rotor device such that the rotor device can rotate with respect to the stator device and having a first opening and a second opening;
a first stator lead and a second stator lead; and
a first slide contact inserted through the first opening to electrically couple to the first stator lead and mechanically couple to the stator device such that the first slide contact contacts the first outer conductive surface at any position relative to the rotor device and a second slide contact inserted through the second opening to electrically couple to the second stator lead and mechanically couple to the stator device such that the second slide contact contacts the second outer conductive surface at any position relative to the rotor device.

12. The rotary device of claim 11 further comprising a first outer insulator surface and a second outer insulator surface, the first outer insulator surface and the second outer insulator surface being positioned in an alternating fashion with the first outer conductive surface and the second outer conductive surface in an axial direction and being positioned radially outward relative to the first outer conductive surface and the second outer conductive surface.

13. The rotary device of claim 11 further comprising a rotor device coupler and a housing configured to cover the rotary device and having a stator housing and a rotor device coupler overmold.

14. The rotary device of claim 11 wherein the first slide contact and the second slide contact are electrically coupled to the first stator lead and the second stator lead, respectively, by press-fit connections.

15. The rotary device of claim 11 wherein the first slide contact and the second slide contact are coupled to the stator device by a press-fit connection.

16. The rotary device of claim 11 wherein the stator device defines a first circumferential groove axially aligned with the first outer conductive surface and a second circumferential groove axially aligned with the second outer conductive surface such that the first stator lead and the second stator lead extend axially along the stator device and circumferentially along the first circumferential groove and the second circumferential groove, respectively.

17. The rotary device of claim 11 wherein the first opening is axially aligned with the first outer conductive surface such that the first slide contact is electrically connected to the first stator lead at a location radially outward from the stator device, extends radially inward through the first opening and contacts the first outer conductive surface at a location radially inward from the stator device.

18. A rotary device comprising:
a rotor shaft configured to rotate around a longitudinal axis;
a plurality of rotor leads;
a plurality of slip ring elements each including a slip ring and an insulator disc having a slip ring portion where the slip ring is positioned and a spacer portion, each of the plurality of slip ring elements including a hub configured to receive the rotor shaft and connected to at least one of the slip ring portion or the spacer portion by at least two support arms, each of the plurality of slip ring elements being electrically coupled to at least one of the plurality of rotor leads;
a stator rotatably coupled to and defining a cavity that is configured to receive the rotor shaft and the plurality of slip ring elements;
a plurality of stator leads;
a plurality of slide contacts mechanically coupled to the stator, the plurality of slide contacts being electrically coupled to at least one of the plurality of stator leads and at least one of the plurality of slip ring elements at any position relative to the rotor shaft and the plurality of slip ring elements; and
a housing configured to cover the rotary device.

19. The rotary device of claim 18 further comprising a rotor device coupler configured to allow rotation of the rotor shaft and the plurality of slip ring elements relative to the stator.

20. The rotary device of claim 18 wherein the stator defines a plurality of slide contact penetrations each axially aligned with one of the plurality of slip ring elements such that each of the plurality of slide contacts is electrically connected to at least one of the plurality of stator leads at a location radially outward from the stator, extends radially inward through one of the plurality of slide contact penetrations and contacts one of the plurality of slip ring elements.

* * * * *